United States Patent [19]
Feindt et al.

[11] Patent Number: 5,848,962
[45] Date of Patent: *Dec. 15, 1998

[54] DEVICE FOR ASSISTING CARDIAC FUNCTION

[75] Inventors: Peter Feindt; Emmeran Gams, both of Homburg/Saar; Uwe Straub, Idar-Obserstein; Arif Kazi, Braunschweig, all of Germany

[73] Assignee: Fraunhofer-Gesellschaft zur Forderung der angewandten Forschung e.v., Munich, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 557,158

[22] PCT Filed: May 27, 1994

[86] PCT No.: PCT/DE94/00605

§ 371 Date: Nov. 22, 1995

§ 102(e) Date: Nov. 22, 1995

[87] PCT Pub. No.: WO94/27552

PCT Pub. Date: Dec. 8, 1994

[30] Foreign Application Priority Data

May 27, 1993 [DE] Germany ............... 43 17 752.2

[51] Int. Cl.$^6$ ................................... A61N 1/362
[52] U.S. Cl. ................................ 600/16; 600/17
[58] Field of Search ................. 600/16, 17, 18; 623/3; 128/903

[56] References Cited

U.S. PATENT DOCUMENTS

| 4,690,134 | 9/1987 | Snyders | 601/153 |
| 5,131,905 | 7/1992 | Grooters | 600/16 |
| 5,569,156 | 10/1996 | Mussivand | 600/16 |

FOREIGN PATENT DOCUMENTS

| 280301 | 8/1988 | European Pat. Off. . |
| 3307211 | 3/1982 | Germany . |

Primary Examiner—John P. Lacyk
Assistant Examiner—Rosiland Kearney
Attorney, Agent, or Firm—Antonelli, Terry, Stout & Kraus, LLP

[57] ABSTRACT

Disclosed is a device for assisting cardiac function having the following features:

at least one half-shell is provided, the interior and exterior contours of which are designed in such a manner that it can be inserted into the human thorax in such a manner that it at least partially surrounds the heart with the exception of the arteries leading to and away from the heart, in or at the half-shell respectively half-shells is situated at least one filling chamber which can be inflated with gas and is propped by the shell, a control unit controls a pneumatic drive which fills and empties the individual filling chambers in such a manner that said filling chambers press at least on the left ventricle synchronously with cardiac activity in such a manner that blood is pressed into the aorta.

16 Claims, 6 Drawing Sheets

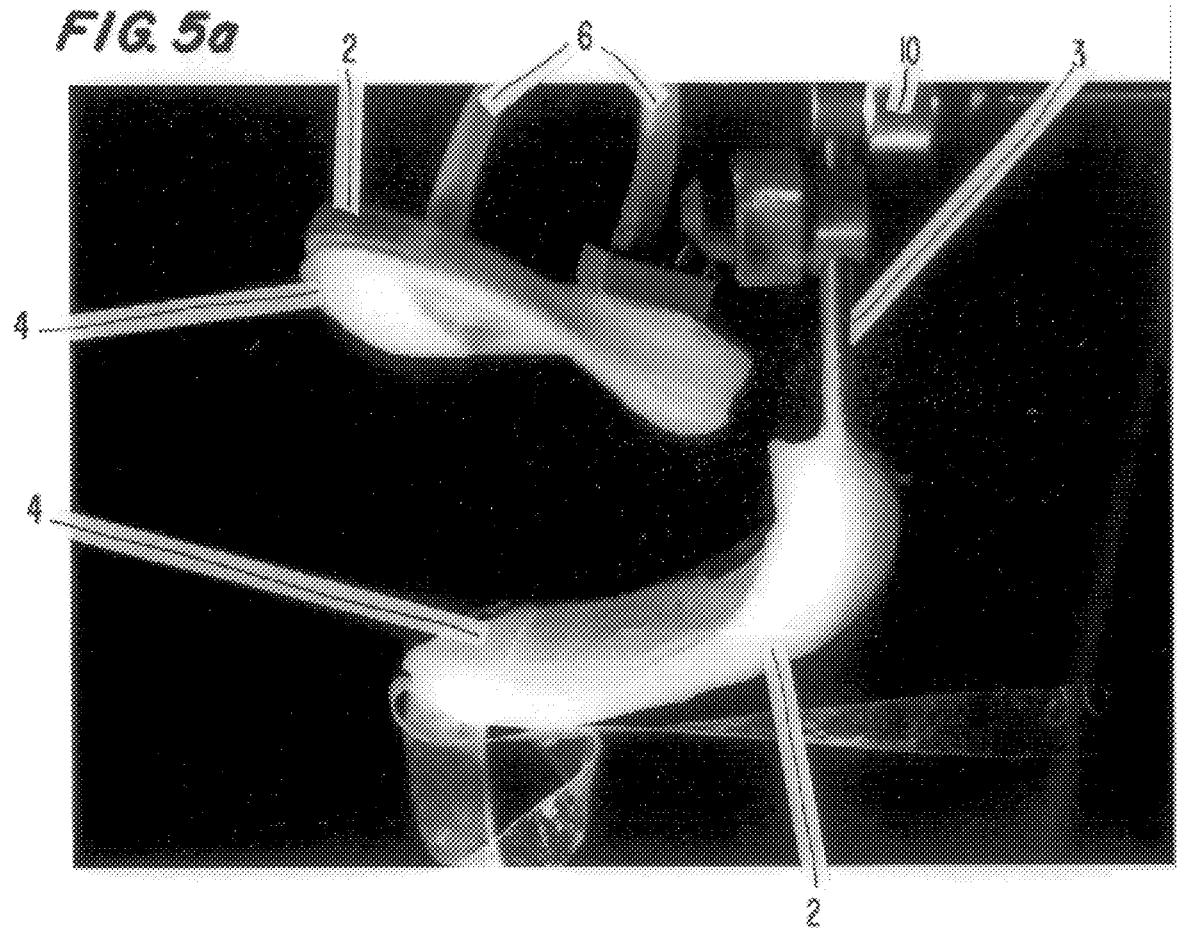

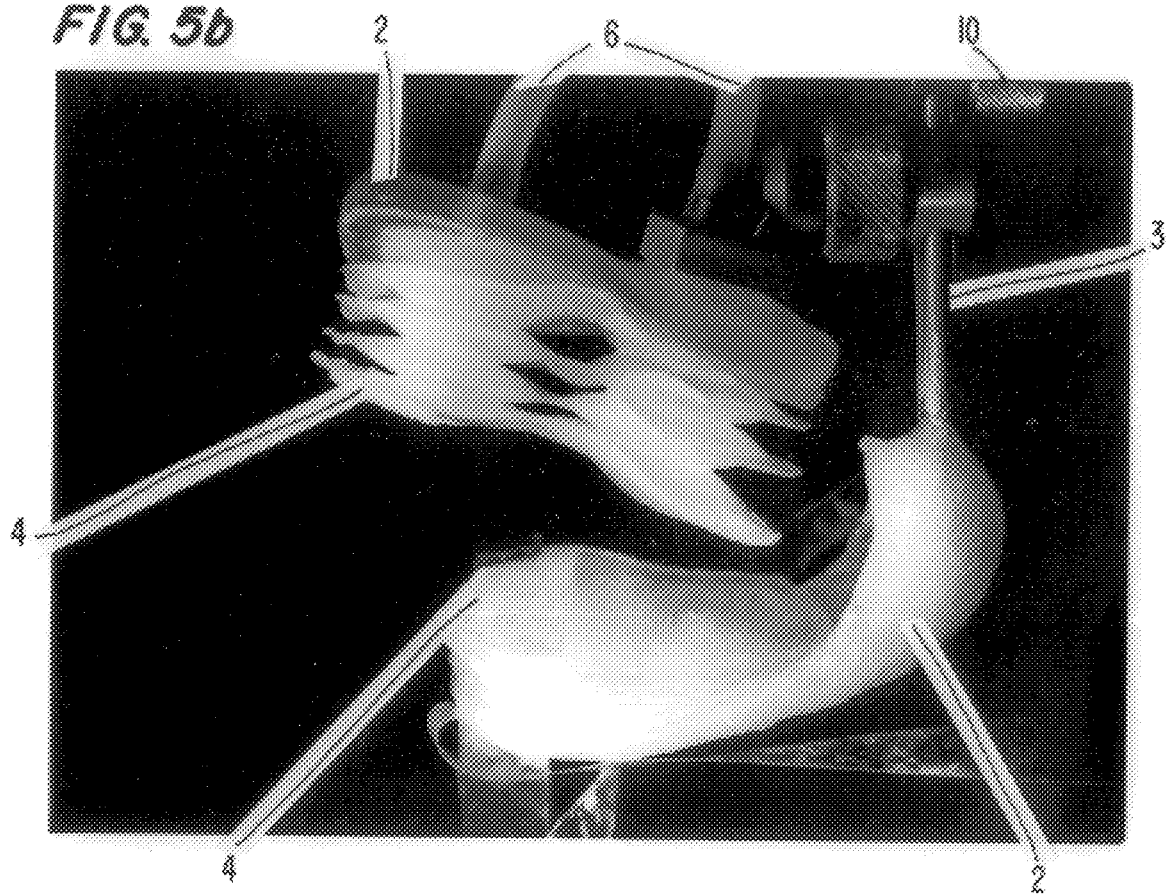

DEVICE FOR ASSISTING CARDIAC FUNCTION

BACKGROUND OF THE INVENTION

1. Technical Field

The present invention relates to a device for assisting the function of the myocardium.

2. State of the Art

When the heart fails to pump, the cause is a muscle weakness of the left ventricle due to which the heart cannot eject sufficient blood volume into the aorta as a consequence of which maintaining circulation is no longer ensured. The reasons for the heart to fail to pump are manifold; to name some examples: virus disease, reduced blood circulation in the myocardium, pumping failure following heart surgery, etc.

Hitherto approaches in treatment of this usually fatal cardiac dysfunction are 1. treatment with medicine
2. treatment with an intra-aortic balloon pump
3. by means of heart transplants
4. by means of so-called muscle ventricles
5. by means of mechanical pump systems connected to the cardiovascular system in place of the left ventricle, ultimately these developments end with the so-called artificial heart.

Medicine can only be used to control cardiac pumping failure if the damage is temporary, because these strong medicines can only be utilized for short periods due to their major side-effects. In particular, however, these medicines can only be employed in minor pumping failure, because only myocardium assistance can be achieved and even medication will not make a manifestly no longer contracting muscle do so. The increase in cardiac performance is only approximately 15%.

Intra-aortic balloon counter pulsation, also called IABP, which was introduced in 1968, is a method in which a balloon catheder is entered into the aorta. Rhythmic inflation and deflation of the balloon increases the diastolic blood flow in the coronary vessels of the heart; the increased supply of blood and the improved blood circulation in the myocardium raises the pump function of the left ventricle. An improvement of approximately 10% to 20% can be achieved with this method. The drawbacks of this method are first only minimal improvement of myocardial pump function, secondly the possibility of complications, mostly bleeding and vessel obstruction. Moreover, as there is a foreign matter in a corporal vessel, the blood has to be prevented from coagulating.

Another approach are heart transplants. According to the reports of the German Association of Thorax-Heart and Vessel Surgery, the number of transplants in Germany has remained relatively constant since 1991. The reason for this ought to be the lack of heart donars. However, the number of patients waiting for a transplant is increasing by approximately 10% annually, without this problem having been solved.

In particular, however, usually only patients with chronic pump failure can be considered for a heart transplant, temporary failure can practically not be treated with this method.

Further disadvantages of heart transplants are the high costs of material and personnel. Moreover, transplant patients have to submit to immune suppression for the rest of their lives, resulting in increased susceptibility to infection. In addition, frequent inpatient treatment to check the implanted organ is required, which is very time and cost consuming.

Finally, now that this method has been established in hospitals for a number of years, it is known that due to the transplant rejection and arteriosclerotic changes in the coronary vessels of the transplanted organs, only unsatisfying long-term results can be achieved. Moreover, the occurence of tumors increases in these patients (i.e., due to immune suppression!).

The so-called muscle ventricles are a surgical procedure in which the large dorsal muscle is lifted and removed and then inserted into the thorax and wrapped around the heart. This dorsal muscle is previously induced by electric instruments to beat permanently which is said to alter the muscle fibers. After this dorsal muscle has been wrapped around the heart and sutured, and it contracts rhythmically, the heart is compressed and thereby the output volume of ejected blood is increased. This approach, which is still in the experimental stage, also has a great number of disadvantages:

1. At this time, it has not been possible to completely and, in particular, not for a sufficient period of time, convert the muscle fibers by means of electric pulses.
2. The entire heart is always compressed thus also the regions which physiologically actually should not be compressed.
3. This method requires major surgery so that temporary pump failure cannot be treated with this method.

Finally, for years attempts have been made to develop an artificial heart which can be implanted where the corporal heart had been and can be connected to the cardiovascular system. However, this has hitherto failed, because the presently available materials indicate very little compatability with the corporal tissue and especially the blood. The coagulation system is badly disturbed when the blood comes into contact with noncorporal surfaces, and hemorrhaging is possible. Medicinal influencing the blood using heparin, which makes blood uncoaguable, also does not offer long-term protection. Repeatedly, blood respectively blood components are destroyed. Consequently the patients have to undergo blood tranfusions at regular intervals (resulting in an increased risk of virus disease infection). Assist systems which can be temporarily connected to the cardiovascular system without removing the heart have been developed parallel to the development of an artificial heart. However, all these systems have in common that they also come into contact with the patient's blood and in this manner blood coagulation is activated on the noncorporal surface. In addition, artificial blood vessels leading to these pump systems and back have to be implanted in the body. Penetration of these noncorporal connections entails that they have to reemerge from the body and therefore harbor great risk of infection.

U.S. Pat. No. 4,690,134 and DE-OS 33 07 211 present devices which assist cardiac function. In both documents, the mycocardial systems are encompassed in the sense of a casing of a container, resulting in even pressure being applied to the entire right low-pressure system of the heart (right atrium and right ventricle) and therefore resulting in completely unphysiological pressing of more than 100 mmHg. A heart cannot cope with this for more than 5 minutes without suffering damage.

SUMMARY OF THE INVENTION

The object of the present invention is to provide a device which, in particular, can assist cardiac function when the heart fails to pump temporarily.

An invented solution to this object is set forth below. Further embodiments of the present invention are the subject matter of further discussions and within the claims.

The present invention is based on the idea of assisting the diseased heart, in particular, the left ventricle by means of mechanical pressure thereon in order to increase in this manner the blood ejected into the aorta and maintain normal blood circulation.

For this purpose, the invented device is provided with the following features:

provided is a shell or parts of shells which are connected to each other, the interior and exterior contour of which is formed respectively contours are formed in such a manner that they can be inserted into the human thorax in such a manner that they at least partially surround the heart in the region of the left ventricle.

in the shell, respectively, in at least one part of the shell, there can be at least one bag provided with at least one or preferably several inflatable air chambers propped by the shell respectively shell parts, a control unit controls a pneumatic drive which fills and empties the individual chambers in such a manner that the bag presses synchronously to cardiac activity at least on the left ventricle and preferably on the left ventricle in such a manner that blood is pressed into the aorta.

With the invented device, cardiac output is raised by a defined pressure on the left ventricle. The resulting counter pressure is distributed evenly by accordingly filled chambers. By cushioning the myocardium, the pressure is evenly distributed in such a manner that injury to the myocardium and the coronary vessels is avoided. The action of the system is synchronized by coupling electric cardiac activity to mechanical cardiac activity.

The energy source of the system and its control unit and the drive can be completely implanted into the body. As most heart diseases resulting in limited pump function are also accompanied by a disturbed cardiac rhythm, it is an advantage if the control unit is provided with a cardiac pacemaker.

The advantage of the invented device over hitherto known solutions is the totally new approach:

The diseased heart is not disconnected from the cardiovascular system, but rather is assisted by the invented device.

Thus the patient's blood no longer comes into contact with foreign surfaces; the problem summarized by the concept of biocompatability does not occur. Another major advantage is that all the parts of the system are implanted into the body and the risk of infection is reduced to a minimum, because conduit penetration is obviated. This also means that the patients do not have to stay in the hospital, but rather can move freely and thereby lower costs enormously.

The invented device can be used in all temporary or manifest structural forms, in which the left (or the right) ventricle is unable, due to myocardial weakness respectively dysfunction, to pump a sufficiently large artery volume (blood volume) with sufficient pressure into the aorta in order to maintain circulation. This dysfunction is totally independent of the cause.

The system can initially be designed for short-term applications. However, if compatability is good, cardiac pump dysfunction of the heart requiring long-term application, can be approached, e.g., all patients waiting for a heart transplant.

Another advantage of the system is that the system, contrary to most other ones employed at this time, if there is an improvement in actual cardiac function, to be expected in short-term application indications, can be slowly reduced and compensated.

In addition, the patients stay mobile, do not have to be treated inpatient, cutting costs drastically.

The device implanted into the thorax is preferably composed of double-walled hard half-shells into which the heart is placed and which can be attached in the region of the outlet of the large vessels from the heart. Naturally, other modes of attachment are also possible. In particular, the hard half-shell, respectively hard half-shells having connecting elements can be designed in such a manner that no other holding means are required, that the device holds itself about the heart. This embodiment is, in particular, preferred in myocardium function assist devices intended for being in the patient's body for a longer period. Thus, this self-holding device is to be preferred if the thorax is to be closed again after surgery.

In order to ensure that the compression unit does not slip toward the axis of the heart, a strap can be placed around the auricles and the blood vessels. However, the resulting pressure force in direction of the cardiac apex must not be ignored, i.e. even if the strap has a relatively large surface, the blood vessels may be cutoff and hinder blood flow.

Straps at the open sides of the compression unit can serve to prevent lateral shifting of the compression unit in relation to the myocardium. Attaching the straps at valve level has much to be recommended, because no major deformations of the myocardium can occur there. However, the valve level moves during contraction of the heart, i.e. the straps should be made of a soft as possible material.

Other possible modes of attachment are, e.g., the attachment of the compression unit to the pericardium below the myocardium or to the sides or attaching it to the thorax.

The outer wall of the half-shell is composed of a firm material, which is not elastic and adapted to the anatomic conditions. The inside layer of the half-shell is composed of an elastic plastic-like material and is subdivided into multiple chambers.

Pressure exertion on the left ventricle occurs by means of pneumatically driven inflation of single or multiple chambers placed over the left ventricle or the right ventricle as well compressing them and in this way causing the blood to eject into the aorta. The resulting counterpressure is compensated by filling the air chambers situated opposite the left ventricle. The drive of the system and the control occur via two separate systems which are implanted subcutaneously in a proven manner and connected via conduit systems to the half-shell respectively half-shells situated around the heart. The control aggregate is additionally coupled to a pacemaker system in order to be independent of a possible cardiac rhythm failure often setting in, caused by many prime diseases accompanied by pumping failure. Cardiac activity is recognized by sensors via the control system, and triggered by this signal, the chamber system is inflated driven pneumatically during cardiac systole. The amount of the inflation and distribution into the individual chambers as well as the temporal components have to be controlled from the outside via already available telemetric systems, thereby ensuring adaption to the acute cardiac activity.

Contraction of the myocardium itself begins at the apex of the heart and continues toward the valve level. The temporal course of pressure application should occur for physiological reasons in the same manner. Natural cardiac movement appears from a flow point of view just as mainly optimum, because when a contraction begins at the cardiac apex, the blood in the ventricles is accelerated from the start in valve direction. At the end of the systole, rapid reduction of the applied pressure must be provided for in order to not hinder filling the ventricles. Pressure applied in this manner can occur by means of the invented device. The needed additional pressure to the pressure prevailing on the outside, which has to be applied to the myocardium is determined by the systolic blood pressure in the left ventricle. As this is approximately 160 mbar, an exterior pressure of 200 mbar should suffice. In any event, a pressure burden of 200 mbar is sufficient.

The pressure in the compression unit should be applied in such a manner that the pressure buildup starts at the apex of the heart and moves away from the cardiac apex. Just prior to when the pressure is reduced again, the pressure chambers have the same even pressure. When the pressure has been completely built up, i.e. it has reached systole, it should be reduced as rapidly as possible. This occurs by applying usually 100 mbar under the ambient pressure to the compression unit.

Insofar as it should remain in the body for a longer period, the setup of the compression unit should be symmetrical, because operation of the system must be independent of the position of the patient's body. A symmetrical setup in this sense means the same number of filling chambers are provided on opposite sides.

The delay in building up the pressure can be realized by a corresponding structural design of the filling chambers. Subdividing the filling chambers on both sides of the myocardium and applying pressure time-delayed to the filling chamber elements has much to be recommended. In the event of serial connection of multiple filling chamber elements, the time delay of the pressure build up has to be optimumly adapted to the given conditions by additional elements, which influence the air supply to the individual filling chamber elements. The realization of the time delay by serial connection of filling chamber elements has the distinct advantage over a corresponding structural design of the filling chamber as a more variable control is made possible.

The typical parameters for the pressure generation unit, which usually are employed with patients, e.g., the pressure buildup of 200 mbar in 60 ms and an average output volume flow of $V_{average}$=200 cm³/s. A maximum output volume flow of $V_{max}$=1000 cm³/s can also be reached.

To sum up, the following are named as advantages:

First of all, the diseased heart is not removed from the cardiovascular system, but rather an attempt is made to replace the contraction power that is lacking by means of pressure from the outside and in this manner assist the heart in its function. Tied to this is the fact that nowhere in the body does blood come into contact with noncorporal surfaces, thereby obviating all biocompatability difficulties. In addition, all the parts of the system are implanted completely in the body so that the risk of infection is reduced to a minimum. The patients are therefore mobile, do not have to be kept under surveillance in inpatient intensive care, which additionally means drastic savings. Blood dilution is therefore also obviated. Due to the inflatability, controlled from the outside, of the individual chambers of the baglike design, adaption of the system to the still present cardiac activity is flexible, thereby permitting possible slow reduction and adaption.

The system should be initially designed for short-term application indications however if compatability is good chronic cardiac dysfunctions can be treated. Therefore, a great number of patients could be treated who today would have to wait in vain for a heart transplant.

By means of the invented device, the left ventricle of the heart can be assisted with a minimum increase in pressure in the right ventricle. An increase in cardiac output of at least 25% is desired. A further development according to the present invention provides for setting the amount of assistance between 0 and 100%. In order to do so, the employed control unit is utilized in conjunction with the pressure generation unit and/or the compression unit in such a manner that the left ventricle of the heart is exposed to pressures of varying force.

BRIEF DESCRIPTION OF THE DRAWINGS

The present invention is described by way of example in the following, without the intention of limiting the scope or spirit of the overall inventive idea, using preferred embodiments with reference to the drawing to which explicitly is referred with regard to the disclosure of all details that are not made more apparent herein. Shown are in.

DESCRIPTION OF THE PREFERRED EMBODIMENTS

Figure 1:
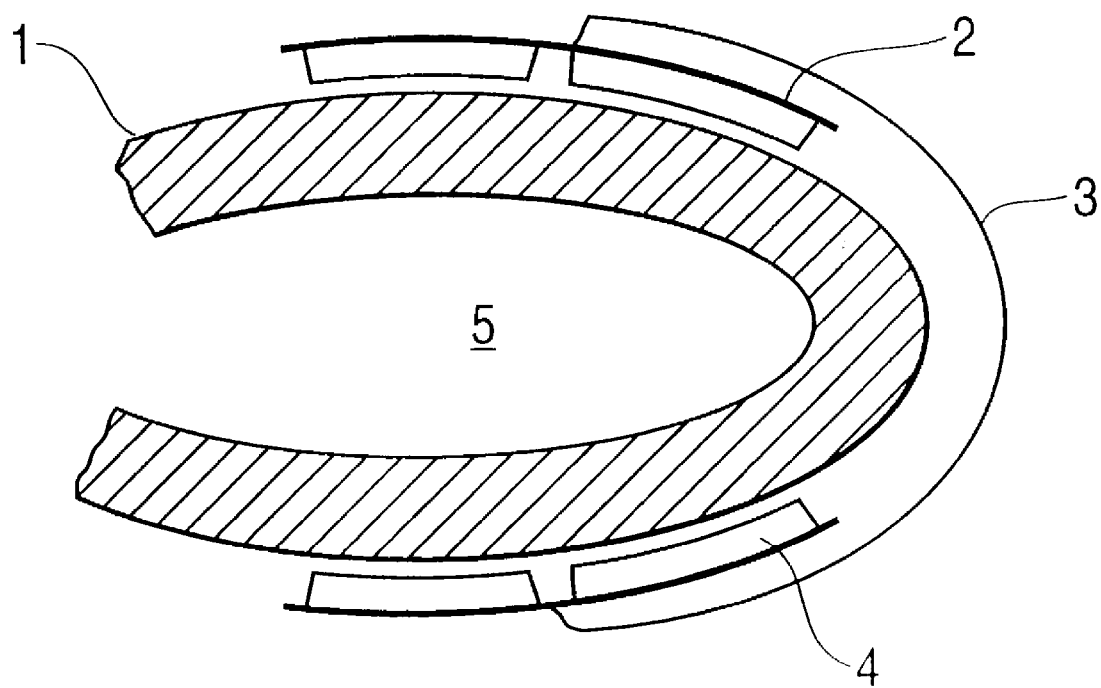
FIG. 1 a heart having the invented device in a cross section of the left ventricle, FIG. 2 a lateral view of the invented device, FIG. 3 a front view of the invented device, FIG. 4 a filling chamber of multiple chamber elements disposed on top of each other, and FIG. 5 an operative compression unit. On the left in an uninflated state and on the right in an inflated state.

In the following figures, the same or corresponding parts bear the same reference numbers obviating renewed introduction and only deviations of the preferred embodiments in these figures from the first preferred embodiment are explained:

FIG. 1 shows a left ventricle (1) and a cross section of the invented device. Left on this drawing is cranial, right is sandal, top is ventral and bottom is dorsal. The invented device is composed of hard half-shells (2), which are connected by means of a connecting element (3). Filling chambers (4) are attached on the hard half-shells and in such a manner that they are aligned to the heart (1).

The hard half-shells (2) and the connecting element (3) should possess high deformation rigidity in order to prevent the filling chambers from slipping out. The connecting element (3) should be adjustable in order to ensure adaptability to the myocardium.

The configuration of the connecting element (3) has to comply with the spatial conditions. For example, connection to the cardiac base is less suited due to poor accessibility because of the blood vessels located there. For this reason, a preferred connection to the sides of myocardium or the apex of the heart is provided.

Pressure buildup at the sides of the myocardium should be avoided in order to keep the increase in pressure in the right ventricle as small as possible. Especially preferred is therefore placing the connecting element at the apex of the heart, because it remains largely stationary during cardiac contraction.

The filling chambers (4) are filled with a gas and emptied again in a desired rhythm assisting the left ventricular muscles (5) in this manner. As a result, the myocardial contraction force is assisted, consequently cardiac function in general is assisted.

Compensating the counterpressure of inflating the filling chambers (4) occurs by means of inflating the filling chambers (4) lying opposite each other.

For simplicity, in the following, the invented device is referred to as IVAD, an acronym derived from intrathoracic ventricular assist device.

Figure 2:
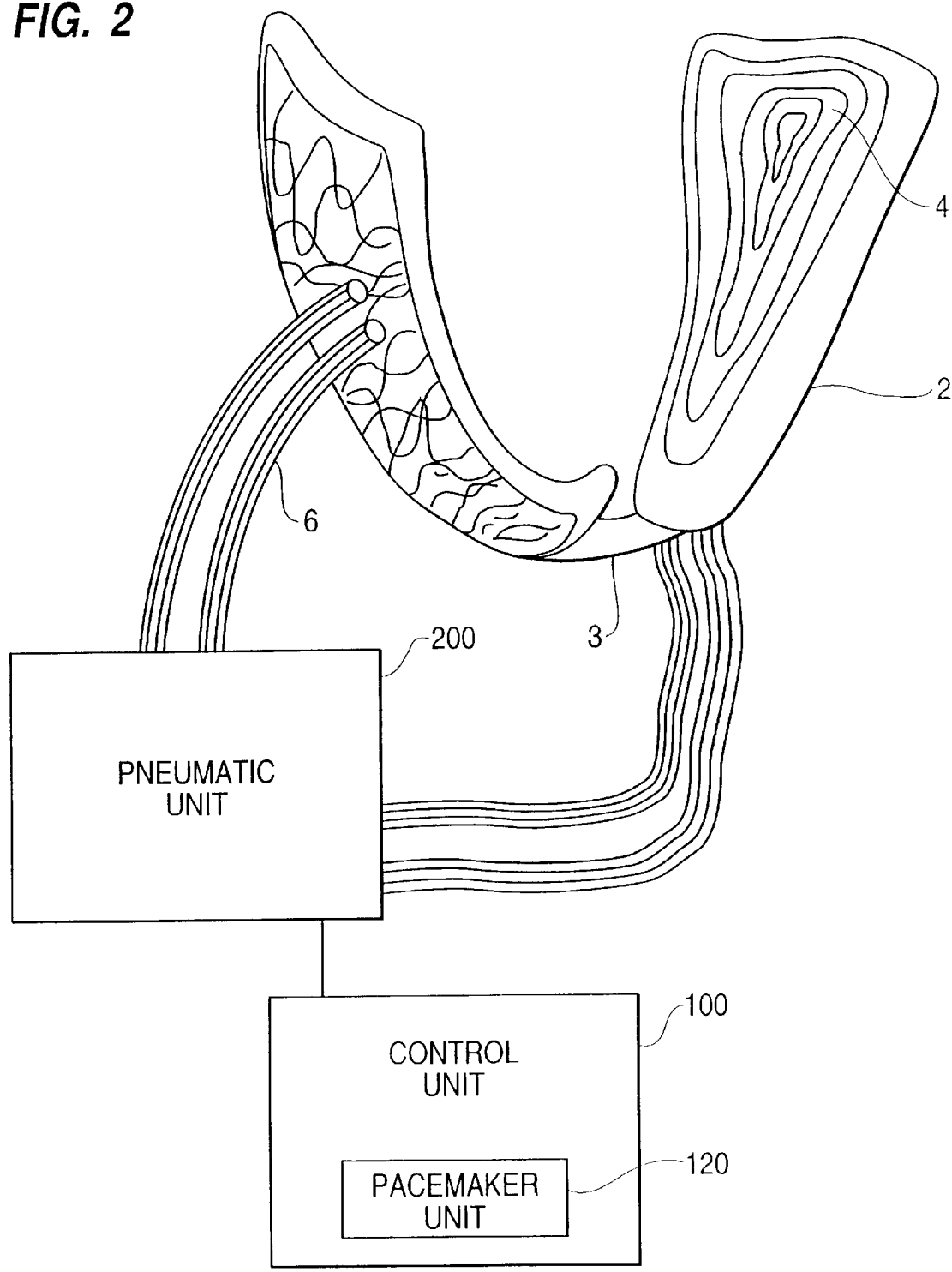

FIG. 2 shows a lateral view of the IVAD and it also illustrates the tong configuration of the IVAD which does not form a complete circle. The gas conduits (6) leading to the filling chambers (4) can be easily recognized. In this way, preferably air can be supplied to and then respectively removed from the filling chambers (4). Further shown is a control unit 100 including a pacemaker unit 120, and a pneumatic unit 200 controlled by the control unit 100.

Figure 3:
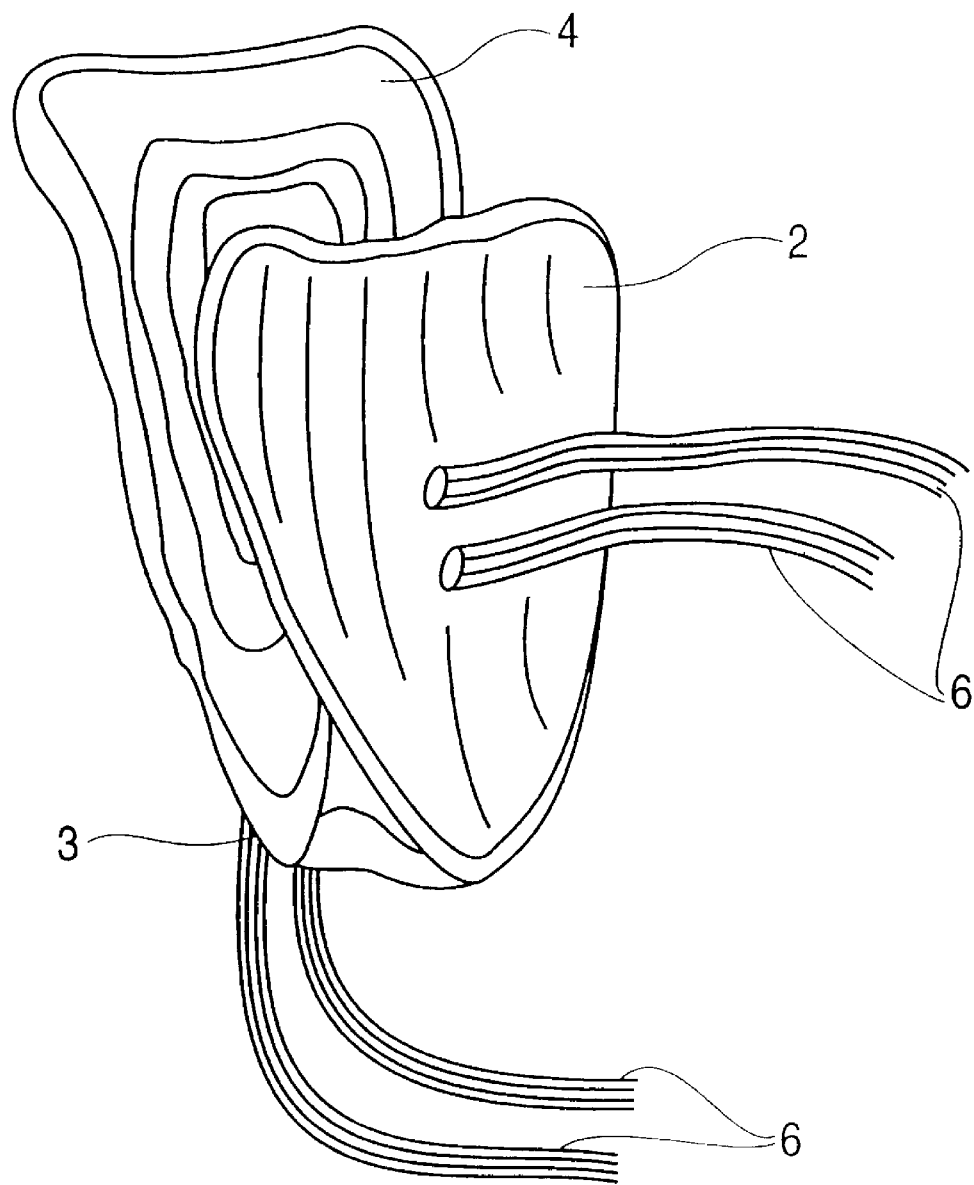

FIG. 3 shows a front view of the IVAD. The hard half-shells are adapted to the shape of the heart (1) and are preferably composed of a biocompatible material.

Figure 4:
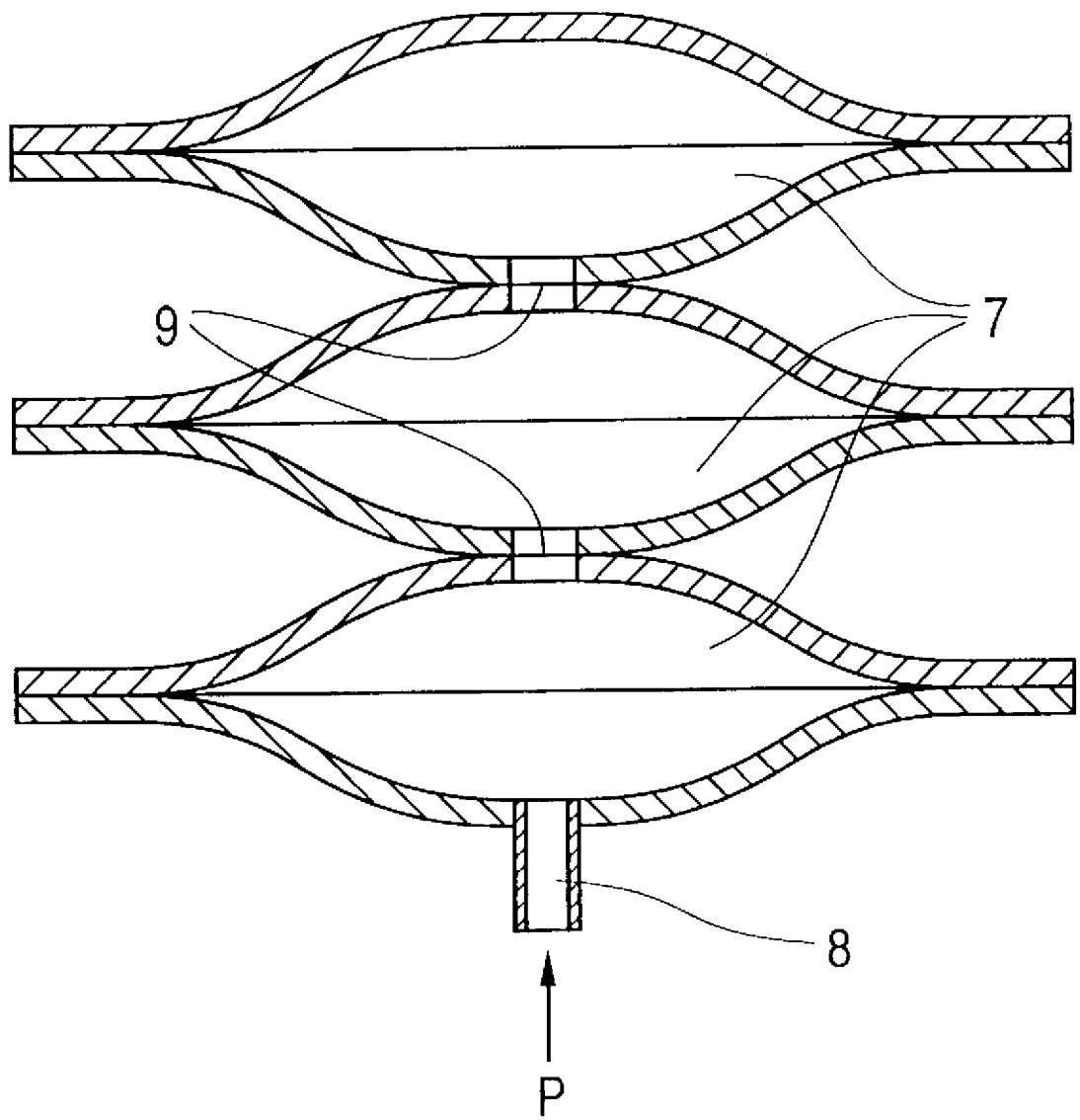

FIG. 4 shows a filling chamber of multiple chamber elements (7) disposed on top of each other. The chamber elements (7) are composed of a biocompatible material such as, e.g., silicone rubber, polytetrafluorethylene (PTFE, 'teflon') or polyurethane (PU). The best material would be one that is very expandable, very thin, very firm and whose expansion is reversible. Polyurethane has proven best suited as a material for the chamber elements (7).

The employed foils of, e.g., PU are either thermally sealed or glued at the ends. FIG. 4 shows in addition a filling tube (8) to which the gas conduits (6) are attached. The individual chamber elements (7) of the filling chamber (4) are connected by openings (9) in such a manner that pressure compensation can occur via the respective chamber elements.

FIG. 5 shows an operative compression unit which was utilized for preliminary tests. On the left side of FIG. 5, the compression unit can be seen in a noninflated state, and on the right side the compression unit is inflated. The additional rods (10) serve the purpose of attaching the compression unit to the thorax clamp separating the thorax. Usually biocompatible materials such as e.g. polymethylmethacrylate (PMMA, 'plexiglass') or fiberglass reinforced plastic on a epoxy basis) are employed as shell material for the hard half-shells (2).

What is claimed is:

1. A device for assisting cardiac function of a heart, comprising:
    a pair of rigidly-interconnected heart tongs having interior and exterior contours and being interconnected by a rigid connecting element, said heart tongs being insertable into a human thorax in such a manner that said heart tongs confront opposing sides of a heart chamber needing assist excluding main arteries leading to and away from the heart;
    at least one filling chamber within the interior contour of at least one tong of said heart tongs, said filling chamber being inflatable with gas while being propped by said tong;
    a control unit which controls a pneumatic drive which fills and empties said filling chamber in such a manner that said filling chamber presses on said heart chamber needing assist synchronously with cardiac activity in such a manner that blood is pressed, and wherein said control unit further comprises a cardiac pacemaker unit;
    wherein said heart tongs and said at least one filling chamber do not form a complete circle.

2. A device according to claim 1, wherein said heart tongs are made of a rigid material which is not deformed by a filling/emptying and pressing of said chamber on said ventricle needing assist.

3. A device according to claim 1 or 2, wherein each tong of said heart tongs has a respective said filling chamber provided therewith.

4. A device according to claim 1, wherein said heart tongs and said connecting element are formed as an integral unit.

5. A device according to claim 1, wherein said control unit and pneumatic drive are designed for subcutaneous implanting.

6. A device according to claim 1, wherein said control unit is designed to be disposed extra-corporally and wherein said pneumatic drive is controllable via a telemetric system.

7. A device according to claim 1, comprising two of said control unit and two of said pneumatic drive for reliability via redundancy.

8. A device according to claim 1, wherein said device is designed such that said heart tongs more specifically confront just a left ventricle of the heart.

9. A device according to claim 1, wherein an amount of assistance provided by said filling chamber being adjustable.

10. A device for assisting cardiac function of a heart, comprising:
    a pair of rigid heart tongs having interior and exterior contours and being rigidly interconnected by a rigid connecting element, said heart tongs being insertable into a human thorax in such a manner that said heart tongs confront opposing sides of a heart chamber needing assist excluding main arteries leading to and away from the heart;
    a filling chamber within the interior contour of each tong of said heart tongs, said filling chamber being inflatable with a gas while being supported by the tong so as to press on an exterior portion of said heart chamber needing assist;
    a control unit which controls a pneumatic drive which fills and empties said filling chamber in such a manner that said filling chamber presses on said heart chamber needing assist synchronously with cardiac activity in such a manner that blood is pressed into an aorta;
    wherein said heart tongs and said filling chamber do not form a complete circle.

11. A device according to claim 10, wherein said control unit further comprises a cardiac pacemaker unit.

12. A device according to claim 10, wherein said tongs are more specifically designed to partially surround one of a left ventricle, right ventricle and a right atrium.

13. A device according to claim 10, wherein said filling chamber is more specifically a multi-chambered filling chamber, and wherein said control unit controls said pneumatic drive to fill different chambers of said multi-chambered filling chamber at differing times so as to apply a pressure buildup which starts at an apex of the heart and which moves away from the apex.

14. A device for assisting cardiac function of a heart, comprising:
    a pair of heart tongs having interior and exterior contours and being rigidly interconnected by a rigid connecting element, said heart tongs being insertable into a human thorax in such a manner that said heart tongs confront only a malfunctioning portion of a heart while not opposing other portions or main arteries leading to and away from the heart;
    at least one filling chamber within the interior contour of at least one tong of said heart tongs, said filling chamber being inflatable with gas while being propped by said tong;

a control unit which controls a pneumatic drive which fills and empties said filling chamber in such a manner that said filling chamber presses on said malfunctioning portion needing assist synchronously with cardiac activity in such a manner that blood is pumped, and wherein said control unit further comprises a cardiac pacemaker unit;

wherein said heart tongs and said at least one filling chamber do not form a complete circle.

15. A device for assisting cardiac function of a heart having a plurality of heart chambers, comprising:

a pair of heart tongs having interior and exterior contours and being rigidly interconnected by a rigid connecting element, said heart tongs being insertable into a human thorax in such a manner that said heart tongs confront opposing sides of a heart chamber needing assist excluding main arteries leading to and away from the heart;

at least one filling assist chamber within the interior contour of at least one tong of said heart tongs, said filling assist chamber being inflatable with gas while being propped by said tong;

a control unit which controls a pneumatic drive which fills and empties said filling assist chamber in such a manner that said filling assist chamber presses on said heart chamber needing assist synchronously with cardiac activity in such a manner that blood is pumped, and wherein said control unit further comprises a cardiac pacemaker unit;

wherein said heart tongs and said at least one filling chamber do not form a complete circle.

16. A device for assisting cardiac function of a heart, comprising:

a pair of rigidly-interconnected heart tongs having interior and exterior contours and being interconnected by a rigid connecting element, said heart tongs being insertable into a human thorax in such a manner that said heart tongs confront opposing sides of a heart chamber needing assist excluding main arteries leading to and away from the heart;

at least one filling chamber within the interior contour of at least one tong of said heart tongs, said filling chamber being inflatable with gas while being propped by said tong;

a control unit which controls a pneumatic drive which fills and empties said filling chamber in such a manner that said filling chamber presses on said heart chamber needing assist synchronously with cardiac activity in such a manner that blood is pressed, and wherein said control unit further comprises a cardiac pacemaker unit;

wherein said heart tongs and said at least one filling chamber do not form a complete circle and are adapted as a confronting arrangement that does not completely encircle a circumference of said heart around ventricles thereof.

* * * * *